United States Patent [19]

Cowie

[11] Patent Number: 4,927,464
[45] Date of Patent: May 22, 1990

[54] PARTICULATE MATERIAL

[75] Inventor: Alan G. Cowie, Stockton on Tees, England

[73] Assignee: Tioxide Group PLC, London, United Kingdom

[21] Appl. No.: 197,169

[22] Filed: May 23, 1988

[30] Foreign Application Priority Data

May 30, 1987 [GB] United Kingdom ............... 8712752

[51] Int. Cl.$^5$ ............................................. C09C 1/36
[52] U.S. Cl. ................................... 106/436; 106/442; 106/481
[58] Field of Search ................... 106/436, 481, 442

[56] References Cited

U.S. PATENT DOCUMENTS

| 3,579,310 | 5/1971 | Lewis et al. |
| 3,728,443 | 4/1973 | Berisford et al. |
| 3,923,968 | 12/1975 | Basque et al. |

FOREIGN PATENT DOCUMENTS

| 0073340 | 7/1982 | European Pat. Off. |
| 0214308 | 4/1985 | European Pat. Off. |
| 49-000450 | 1/1974 | Japan . |
| 52-72833 | 6/1977 | Japan . |
| 53-124627 | 10/1978 | Japan . |
| 54-073193 | 6/1979 | Japan . |
| 55-154317 | 7/1979 | Japan . |
| 57-067681 | 6/1982 | Japan . |
| 58-043912 | 3/1983 | Japan . |
| 58-62106 | 4/1983 | Japan . |
| 59-62517 | 4/1984 | Japan . |
| 59-98009 | 6/1984 | Japan . |
| 59-172415 | 9/1984 | Japan . |
| 59-223231 | 12/1984 | Japan . |
| 61-097133 | 9/1985 | Japan . |
| 60-186418 | 9/1985 | Japan . |
| 458535A2 | 7/1979 | U.S.S.R. |
| 1256341 | 1/1969 | United Kingdom . |
| 1387218 | 3/1975 | United Kingdom . |
| 1479988 | 7/1975 | United Kingdom . |
| 1541621 | 3/1979 | United Kingdom . |

Primary Examiner—A. Lionel Clingman
Assistant Examiner—Willie J. Thompson
Attorney, Agent, or Firm—Banner, Birch, McKie & Beckett

[57] ABSTRACT

There is an increasing demand for products which are effective in the absorbancy of UV light but still remain transparent to visible light. Titanium dioxide has been proposed for this use.

A new form of titanium dioxide has been developed which is very effective in use and which is acicular in shape and having a ratio of the largest dimension to the shortest within the range 8:1 to 2:1 and wherein the largest dimension is from 0.01 to 0.15 micron and in which the particles have a coating of a hydrous oxide of aluminium and of silicon in a weight ratio of at least 1.5 and not greater than 4.5 expressed as the oxides. The materials are eminently suitable for use in cosmetics and other skin care products.

17 Claims, 1 Drawing Sheet

PARTICULATE MATERIAL

This invention relates to particulate material and particularly to material which is suitable for use as an absorber for UV radiation.

According to the present invention particulate material comprises titanium dioxide the particles of which are acicular in shape and have a ratio of the largest dimension to the shortest within the range 8:1 to 2:1 and wherein the largest dimension is within the range 0.01 to 0.15 micron and said particles having a coating comprising an oxide or hydrous oxide of aluminium and an oxide or hydrous oxide of silicon in a weight ratio of $Al_2O_3:SiO_2$ of at least 1.5 and not greater than 4.5 and said material being substantially transparent to visible light and substantially absorbant to UV light.

Figure 1:
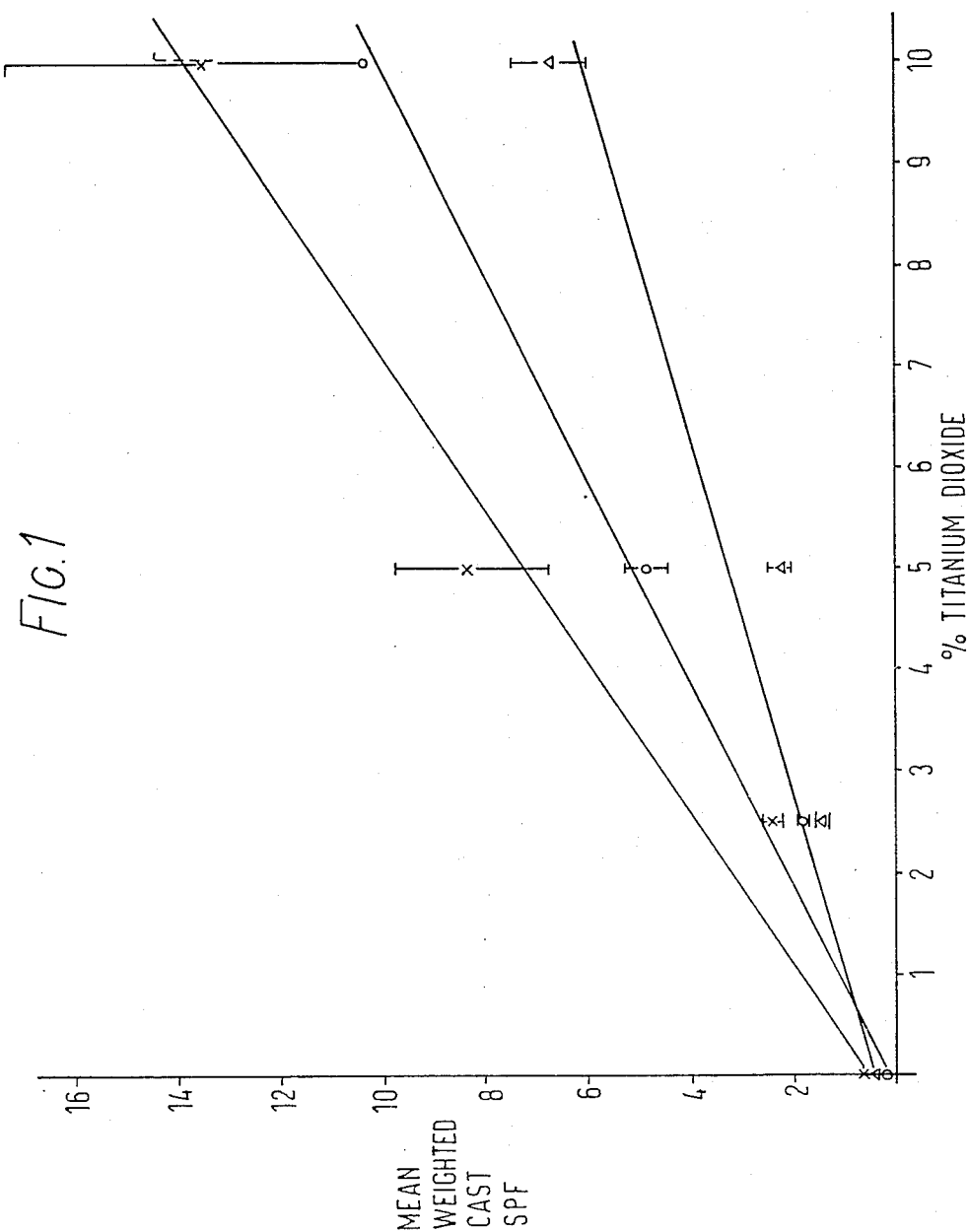
FIG. 1 shows the weighted SPF (sun protection factor) for three compositions containing three different titanium dioxide particulate materials plotted against the amount of titanium dioxide in the compositions.

The material of the present invention comprises particles of titanium dioxide which may be of the rutile, anatase or amorphous form and each particle may be composed of aggregated smaller particles or crystals or ideally each particle is a single particle of the size chosen to be advantageous.

Generally speaking the largest dimension of the particles of titanium dioxide is within the range 0.01 to 0.15 micron and preferably is within the range 0.02 to 0.1 micron. In the acicular product the ratio of largest dimension to the shortest dimension is from 8:1 to 2:1.

Also preferably whilst the particles of titanium dioxide have sizes within the specified range of dimensions the particles do exhibit a narrow size distribution. For the most preferred particles it is most advantageous that at least 80 per cent have a size within the range of largest dimensions of 0.01 to 0.15 micron.

The materials of the present invention are coated with an oxide or hydrous oxide of aluminium and with an oxide or hydrous oxide of silicon in a specified weight ratio of $Al_2O_3:SiO_2$ of at least 1.5 and not greater than 4.5. Preferably the weight ratio $Al_2O_3:SiO_3:SiO_2$ in the coating is from 2.0 to 3.5.

The actual amount of the coating present is such that the amount of oxide or hydrous oxide of aluminium when expressed as $Al_2O_3$ is from 1.0 to 30.0 weight percent based on weight of titanium dioxide and preferably from 5.0 to 20.0 weight per cent $Al_2O_3$ on weight of titanium dioxide. Consequently the amount of oxide or hydrous oxide of silicon will be that necessary to maintain the ratio of the amounts of coating oxides or hydrous oxides within the specified range and generally speaking the weight of oxide or hydrous oxide of silicon will be within the range 0.2 to 20.0 weight percent as $SiO_2$ based on titanium dioxide and preferably from 1.5 to 7.0 weight percent.

If desired the particulate material may carry a coating of one or more organic materials such as an organic silicon compound e.g. a polymeric organic silicon compound. Other organic coating agents which may be present are the polyols, amines, or alkanolamines.

The particulate material of the present invention may be formed by any suitable process for making acicular products. Typical processes may involve hydrolysis of an appropriate titanium compound such as titanium tetrachloride or an organic or inorganic titanate or oxidation of an oxidisable titanium compound for example in the vapour state.

A typical process involves the preparation of a solution of a soluble titanium salt which is then hydrolysed to form hydrous titanium oxide. The solution can be that obtained in the so-called "sulphate" process for the manufacture of titanium dioxide pigment in which a titaniferous ore is digested with concentrated sulphuric acid and the digestion cake dissolved in water or dilute acid to produce a solution of titanyl sulphate. During the process additional process stages of classification and reduction are usually employed. Hydrolysis of the titanyl sulphate solution produces the precipitate of hydrous titania which is sometimes called "pulp". Soluble iron compounds remain in solution and after neutralisation and washing to an appropriate degree of impurity level the precipitated pulp of hydrous titania is treated with, say sodium hydroxide and subsequently hydrochloric acid to produce the acicular titanium dioxide.

Usually prior to coating of the acicular titanium dioxide product it is preferred to mill the product to an appropriate particle size falling within that specified hereinbefore. Milling conveniently can be effected in a wet milling process employing a grinding medium such as sand which can be separated easily and effectively from the milled pulp. Milling, preferably, as carried out in the presence of a dispersing agent such as an alkali metal silicate, e.g. sodium silicate, which provides at least some of the source of the coating hydrous silica deposited subsequently. Should another dispersant be used for example, an organic dispersant, then the source of coating hydrous silica is added subsequently.

The precipitated product is then treated to deposit the hydrous silica and hydrous alumina in the specified amounts and proportions. To an aqueous dispersion of the product containing a hydrolysable salt of aluminium and usually a silicate there is added a reagent which effects hydrolysis of the salt of aluminium and of the silicate to form hydrous alumina and hydrous silica. Typically aluminium sulphate can be the source of alumina or alkaline aluminate can be employed or indeed both an acidic aluminium salt and an alkaline solution of an aluminate can be added either together or sequentially.

Depending on the pH of the dispersion of the product hydrolysis and precipitation may require the addition of an alkali or an acid as the reagent. Preferably coating is effected by adding to an acid reacting dispersion of the product containing an alkali metal silicate an amount of aluminium sulphate followed by an amount of an alkali metal aluminate prior to the addition of a mineral acid such as sulphuric acid to effect formation and precipitation of hydrous alumina and adjustment of the pH of the dispersion to a value in the range 6 to 8, preferably pH 6.8 to 7.5.

The coated produce is separated from the aqueous dispersion and after washing is dried at an elevated temperature to say 70° C. to 100° C. In contrast to the usual "sulphate" process for the production of pigmentary titanium dioxide no calcination of hydrous titania is carried out prior to coating. Consequently it may be that some of the titania in the product of the invention, if prepared from pulp, is present in a hydrous form even after drying.

Alternatively the particles of titania to be coated according to the present invention can be prepared by decomposition or hydrolysis of suitable titanium compounds. Typically high temperature hydrolysis of an organic titanium compound such as a titanium alkoxide can be used to produce a fine particle sized titania pulp to be converted to acicular form. Oxidation or hydrolysis in the vapour state of titanium halides under appropriate conditions can be also used to prepare the titania to be coated.

The products of the present invention have the property of absorbing UV light and transmitting visible light. This means that the products can find use in a wide variety of applications wherein it is important to maintain transparency of visible light while substantially preventing transmission of UV light to a surface. Cosmetics, sun-creams, plastics films and wood coating and other coating compositions are just a small number of applications for the products.

Generally speaking the coating present on the particles has the effect, amongst others, of affecting the dispersibility of the particles in various media and the absorbancy of UV light by the particles is also altered by the presence of the coating. Usually the particle absorbancy is expressed as a function of the amount of the uncoated particle and when expressed as an extinction coefficient is substantially independent of a medium in which the particles are dispersed. However the extinction coefficient is preferably measured at various wave-lengths of light. Generally speaking uncoated particles of the present invention have at least a minimum extinction coefficient when adequately dispersed of at least 30 liters per gram of uncoated product per cm at a wave-length of 308 nm. Preferably the dispersion has a minimum extinction coefficient of at least 35, and more preferably greater than 40 liters per gram of uncoated product per cm at a wave length of 308 nm.

The coating reduces the photo-reactivity of the product which otherwise is of reduced suitability for use, particularly in cosmetic preparation. However the presence of a coating does tend to reduce the absorbance of the product.

The products of the invention can be in the dry state or sold or further handled in the form of a dispersion in either water or in another medium.

The most preferred dispersions are prepared by milling the coated product of the invention in a chosen media until the extinction coefficient has reached the desired value. A very useful product is obtained by milling in a liquid oil e.g. a base medium of a cosmetic or sun-burn cream or ointment in the presence of a dispersant.

The oil can be any oil which is desirably present in the resultant dispersion. Such oils usually are the vegetable oils, for example, fatty acid glycerides, fatty acid esters and fatty alcohols with typical examples being sunflower oil (fatty acid triglyceride), castor oil, oleic and linoleic glycerides, saturated fatty acid di-esters e.g. octyl -dodecyl stearoyl stearate, oleyl alcohol, and isopropyl palmitate, pentaerythritol tetracaprylate/caprate, propylene glycol di-esters of coconut fatty acids and pentaerythritol tetraisostearate.

The mill which is employed to effect the grinding of the titanium dioxide product in the oil is one which uses a particulate grinding medium to grind the product. Such mills are bead mills equipped with one or more agitators and using sand or glass beads or ceramic beads or other particles as the particulate grinding medium. Particularly useful are those mills which operate at a high speed and depending on the size of mill a speed of the order of 2500 rev. per minute (r.p.m) is not unusual. For instance mills operating at a speed of from 1000 r.p.m to 6000 r.p.m are suitable. Agitator mills in which the tip speed of the agitator is up to and can exceed 10 meters/sec are of use. If desired the mill can be cooled. Also the dispersions can be pre-mixed using a high speed stirrer or the oil can be added to the mill initially and then the titanium dioxide and the organic dispersant co-added to the oil subsequently. After milling has been carried out for the required time the dispersion is separated from the grinding medium.

the dispersions include an organic dispersing agent to promote the dispersion of the particulate titanium dioxide in the chosen oil. Many types of organic dispersing agent have been developed and are available for use in promoting the dispersion of particles in oily media e.g. substituted carboxylic acids, soap bases and polyhydroxy acid. Typically the dispersing agent can be one having a formula X.CO.AR in which A is a divalent bridging group, R is a primary secondary or tertiary amino group or a salt thereof with an acid or a quaternary ammonium salt group and X is the residue of a polyester chain which together with the —CO—group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxystearic acid small amounts of stearic acid and palmitic acid.

Dispersing agents based on one or more polyesters or salts of a hydroxycarboxylic acid and a carboxylic acid free of hydroxy groups can also be used. Compounds of various molecular weight can be used.

Other suitable dispersing agents are those monoesters of fatty acide alkanolamides and carboxylic acids and their salts based on 6-226 (un)saturated fatty acids. Alkanolamides are based ethanolamine, propanolamine or aminoethyl ethanolamine for example. Alternative dispersing agents are those based on polymers or copolymers of acrylic or methacrylic acids e.g. block copolymers of such monomers.

Other dispersing agents of similar general form are those having epoxy groups in the constituent radicals such as those based on the ethoxylated phosphate esters.

The dispersing agent can be one of those commercially referred to as a hyper dispersant and specifically available as such.

Also it has been found to be advantageous in preparing the uncoated base of the products of the invention that the product prior to coating should have been washed to reduce the impurity level of the base to a most desirable level. Accordingly it is desirable that the uncoated base product should have a purity such that the amount of sulphate in the uncoated base does not exceed 0.9% by weight expressed as $CO_3$ on weight of base product.

It has also been found to be advantageous that the filtrate from the final wash should have a conductance of less than 147 micro mhos.

The invention is illustrated in the following Examples.

EXAMPLE 1

Ilmenite was digested with concentrated sulphuric acid. The digestion cake obtained was dissolved in water to form a crude liquor containing iron and titanium sulphates and some suspended insoluble matter. Any iron present in the ferric form was reduced chemically prior to filtering insoluble matter. The liquor after any necessary crystallisation and filtration was concentrated by vacuum treatment and then hydrolysed to precipitate hydrous titanium dioxide by boiling and addition of any necessary reaction agent. The product on filtering was a pulp of uncoated hydrous $TiO_2$.

In the subsequent process any water added or used was taken to be demineralised water.

The pulp of the uncoated hydrous $TiO_2$ obtained was diluted to a concentration of 280 grams per liter $TiO_2$ and a sample amount of 2.5 liters taken and heated to 60° C. Aqueous sodium hydroxide solution containing 700 grams per liter NaOH in an amount of 1.5 liters was heated to 90° C. and then transferred to a reaction flask having a volume of 5 liters fitted with a condenser. The hot diluted pulp was added over a period of 30 minutes to the reaction flask whilst agitating the contents vigorously and the mixture temperature was held at 117° C. whilst agitating for a period of 2 hours after the addition had been completed. Cold water was added to quench the solution in the flask to 90° C. and to decrease the concentration of titanium dioxide to 140 grams per liter. The amount of water added was approximately 20% of the total volume achieved. The contents were agitated for a further 15 minutes at this temperature of 90° C. prior to cooling to a temperature of 50° to 55° C. by the addition of a further amount of cold water which reduced the concentration of titanium dioxide to about 80 to 90 grams per liter. The dispersion was filtered and the filter cake washed with warm water at a temperature of 50° C. to 60° C. so that the filtrate contained less than 1500 ppm $Na_2O$. The washed filter cake was then re-slurried in water to a concentration of 200 grams per liter $TiO_2$ and at this stage the product was sodium titanate.

Two liters of the washed sodium titanate was added to a reaction flask having a volume of 6 liters and fitted with a condenser. The pH of the dispersion in the flask was reduced to a value within the range 2.8 to 3.1 by the addition of aqueous hydrochloric acid (30% w/w) and the mixture then heated to a temperature of 60° C. at the rate of 1° C. per minute. The pH of the mixture was rechecked and adjusted, if necessary, to a value within the range 2.8 to 3.1 by a further addition of the aqueous hydrochloric acid. The dispersion was held at this temperature for 30 minutes whilst agitated. A further quantity of hydrochloric acid was then added such that the volume added was 0.754 liters of 30% HCl acid per kilogram of $TiO_2$ in the dispersion such that the ratio of $HCl/TiO_2$ equalled 0.26. The slurry was then heated to the boiling point over a period of 40 minutes and held at the boiling point for a period of 90 minutes whilst being agitated. The treated product was then quenched by addition of two liters of water and the dispersion had a pH value of 0.4. Sodium hydroxide solution at a concentration of 400 grams per liters NaOH was then added to neutralise the dispersion to a pH of 7.5 and approximately 460 ml of the aqueous sodium hydroxide was required. The dispersion was filtered and the filter cake washed with two liters of water. The washed filter cake was then redispersed with a further quantity of two liters of water and filtered again to produce a filter cake having a solids content of 34% by weight.

882 grams of the filter cake (300 grams $TiO_2$) was diluted to a concentration of 100 grams per liter $TiO_2$ with demineralised water and mixed with sodium silicate in an amount equivalent to 5% by weight $SiO_2$ on weight of $TiO_2$ and milled in a sand mill for 2 hours after adjusting the pH of the dispersion to 10.0 to 11.5 with aqueous sodium hydroxide. The grinding medium was Ottowa sand and was removed from the milled dispersion at the end of the milling period by filtration.

The aqueous dispersion after removal of the sand had a pH of 9.1 and was heated to 60° C. and maintained at this during the coating operation.

To the stirred dispersion aqueous aluminium sulphate solution (68 grams per liter $Al_2O_3$ equivalent) was added dropwise in an amount sufficient to introduce aluminium sulphate in an amount equivalent to 5% $Al_2O_3$ on weight of $TiO_2$ over a period of 60 minutes. Approximately 219 mls of the solution were added. After the addition has been completed the dispersion had a pH of 2.4 and was allowed to age for 30 minutes at 60° C. whilst stirring was maintained.

An alkaline solution of sodium aluminate (80 grams per liter $Al_2O_3$) was then added over a period of 60 minutes to the stirred dispersion in an amount sufficient to introduce the equivalent of 10% by weight $Al_2O_3$ on weight of $TiO_2$. Approximately 375 mls of the solution was found to have been added. The dispersion which had a pH of 11.8 was stirred at 60° C. for 45 minutes.

Sulphuric acid (10%) was added to the aqueous dispersion to reduce the pH to 7.5. The neutralised dispersion was aged for 15 minutes whilst being stirred. The dispersion was filtered to produce a filter cake of the coated product which was then washed with 1 liter of demineralised water. The cake was redispersed in 1 liter of demineralised water, re-filtered and then washed again with demineralised water.

The product was dried at 110° C. overnight. The product was acicular rutile titanium dioxide having an average size of $0.02 \times 0.10$ microns with a coating of hydrous silica in an amount equivalent to 4.8% by weight $SiO_2$ and $TiO_2$ and hydrous alumina in an amount of 11.2% by weight $Al_2O_3$ on $TiO_2$ as determined by analysis of the product.

The product was tested in aqueous media by adding 1.25 grams of the product to 25 ml of a 1/16% by weight solution of sodium silicate in demineralised water. The pH was adjusted to 10.5 to 11.0 by the addition of aqueous sodium hydroxide and the dispersion milled in a small bead mill for 2 hours with 50 grams of glass beads known as Ballotini as the grinding medium.

The mill base so obtained was removed from the mill and grinding medium and diluted with demineralised water in the proportion 0.1 ml mill base to 500 ml water.

The mill base was then exposed in a spectrometer (Beckman DU-50) with a 1 cm path length and the absorbance of UV and visible light measured. Extinction coefficients at two wave lengths were calculated from the equation $A = E.c.l$ where $A$ = absorbance, $E$ = Extinction coefficient in liters per gram per cm, $c$ = concentration in grams per liter and $l$ = path length in cm.

The results were

| E (524 nm) | E (308 nm) | E (max) | λ (max) |
|---|---|---|---|
| 1.2 | 50.6 | 57.6 | 285 | where λ is the wavelength.

A further sample of the dried product of the Example was tested in sunflower oil. 50 grams of the dry product was added with 70 mls of sunflower seed oil (density = 0.93) and 5.0 gram of a dispersant being a polyhydroxy stearic acid known as Solsperse 3000 to a high speed bead mill (Eiger M-50-VSE) with 60 grams of 1 mm glass beads as grinding aid. The dispersion was milled for 3 hours.

After separation from the grinding aid a portion (0.1 gram) of the milled dispersion was diluted with n-hexane (100 ml). This diluted sample was then further diluted with n-hexane in the ratio sample:n-hexane of 1.19. The total dilution was 1:20,000.

The absorbance of UV and visible light was measured as described above and the Extinction coefficient at the two wavelengths calculated as follows:

| E (524 nm) | E (308 nm) | E (max) | λ (max) |
|---|---|---|---|
| 4.0 | 42.3 | 43.9 | 285 |

A further sample of the dried product was prepared in the form of a polymer masterbatch containing 20% by weight of the product and polyethylene (Alkathene 017/640) by melt-mixing at 120° C. in a mixer known as a Brabender Plasti-Corder.

Polypropylene (BP DYNH-3) was the added to the masterbatch by melt mixing at 170° C. to ½ per hundred resin (pHr) and 100 um films extruded.

The absorbance of UV and visible light by the films was measured directly and were as follows:

| A (524 nm) | A (308 nm) | A (max) | λ (max) |
|---|---|---|---|
| 0.12 | 1.34 | 1.41 | 297 |

EXAMPLE 2

The experiment described in Example 1 was repeated except that the product was coated with a hydrous oxide of silicon in an amount of 2% by weight $SiO_2$ and with a hydrous oxide of aluminium in an amount of 6% by weight $Al_2O_3$ on $TiO_2$ by changing the amounts appropriately of the coating reagents.

The product was tested as described in Example 1 and the results of dispersion in water and in sunflower oil are given below.

| E (524 nm) | E (308 nm) | E (max) | λ (max) |
|---|---|---|---|
| \multicolumn{4}{c}{$H_2O$ Dispersion} | | | |
| 3.0 | 53.1 | 59.2 | 295 |
| \multicolumn{4}{c}{Sunflower Oil Dispersion} | | | |
| 2.9 | 49.0 | 51.3 | 292 |

EXAMPLE 3

A solution of titanium tetrachloride in hydrochloric acid having an acid/titanium ratio (weight ratio) of 1.77 was prepared containing 200 grams per liter $TiO_2$ equivalent. An aqueous solution of sodium hydroxide (110 grams per liter) was prepared from carbonate free ingredients.

To a 3 liter glass flask fitted with a stirrer there was added 1203 ml of the aqueous sodium hydroxide solution and 400 ml of water (demineralised). To the stirred solution there was then added 400 mls of the titanium tetrachloride solution over a period of 15 minutes and during this period the stirrer speed was controlled at 100 rev. per minute. After the addition had been completed the temperature was raised from its initial value of 40°-45° C. to 82° C. at a rate of 1° C. per minute and the mixture was held at this temperature for a further 120 minutes while stirring continued. During the heating to the temperature of 82° C. the solution was observed to clear partially, normally at about 60°-70° C. as the titanium dioxide peptises and then re-precipitates.

After holding at 82° C. for 120 minutes the mixture was added to 2.5 liters of cold distilled water to quench the mixture then a further 5 liters of the water at 60° C. is added to the quenched mixture. Sodium hydroxide solution (110 grams per liter) is then added to the mixture to neutralise the mixture to a pH value of 7.5. The neutralised and flocculated mixture is allowed to settle, filtered and the cake washed with 2.5 liters of water by stirring prior to refiltering. The cake is washed again by re-slurrying with 2.5 liters of water and filtered to produce a cake having a solids content of 22% by weight.

The titanium dioxide in the cake was acicular and rutile having an average size of 0.01 to 0.05 microns.

The acicular titanium dioxide product obtained was coated in accordance with the precedure of Example 1 with hydrous silica in an amount of 4% by weight and hydrous alumina in an amount of 12% by weight on weight of $TiO_2$.

Dispersions in water, sunflower oil and in polypropylene were prepared as described in Example 1 and tested. The results are given below.

| E (524 nm) | E (308 nm) | E (max) | λ (max) |
|---|---|---|---|
| \multicolumn{4}{c}{$H_2O$ Dispersion} | | | |
| 0.6 | 35.3 | 48.2 | 280 |
| \multicolumn{4}{c}{Sunflower Oil} | | | |
| 0.4 | 35.0 | 51.5 | 280 |

| A (524 nm) | A (308 nm) | A (max) | λ (max) |
|---|---|---|---|
| \multicolumn{4}{c}{Polypropylene} | | | |
| 0.02 | 1.53 | 1.82 | 280 |

EXAMPLE 4

The experiment described in Example 1 was repeated except that the product was coated with hydrous silica in an amount of 5 per cent by weight as $SiO_2$ and hydrous alumina in an amount of 15 per cent by weight on $Al_2O_3$.

dispersions were prepared in water (solids content 4.8%) and in an oil (isopropyl palmitate) (solids content 40% $TiO_2$) and tested as described in Example 1. The results are given below:

| E (524 nm) | E (308 nm) | E (max) | λ (max) |
|---|---|---|---|
| \multicolumn{4}{c}{$H_2O$ Dispersion} | | | |
| 1.4 | 49.6 | 57.0 | 285 |
| \multicolumn{4}{c}{Oil Dispersion} | | | |
| 2.9 | 45.6 | 46.8 | 296 |

Samples of the oil dispersion were formed into three sunscreens compositions A, B and C from ingredients tested below.

| | | % by weight | | |
|---|---|---|---|---|
| Item | | A | B | C |
| 1 | Polyglycol cetostearate (Tefose 1500) | 10.0 | 15.0 | 5.0 |
| 2 | Light liquid paraffin (WOM14) | 2.0 | 2.0 | 2.0 |
| 3 | Polyglycol C12-C18 Triglycerides (Labrafil M2130 CS) | 3.0 | 4.0 | 2.0 |
| 4 | Stearic acid | 1.0 | 1.0 | 1.0 |

| | | % by weight | |
|---|---|---|---|
| Item | A | B | C |
| 5 Glycerin BP | 3.0 | 3.0 | 3.0 |
| 6 Titanium dioxide (TiO₂) dispersion | 12.5 | 25.0 | 6.25 |
| 7 Water | 68.5 | 50.0 | 80.75 |
| % TiO$_2$ | 5 | 10 | 2.5 |

Generally the sunscreen composition was prepared in a beaker using a colloid mill (Silverson). Items 1, 6, 2, 3 and 4 were heated to 70° C. and then milled until a homogeneous mixture obtained. Items 5 and 7 were heated in a separate beaker to 70° C. and then slowly added to the beaker. After the addition had been completed the milling was continued for a period of 10 minutes. The sunscreen composition was then allowed to cool under gentle stirring.

The compositions were then tested to determine the sun protection factors (SPF) using the in vitro Luviset cast method described in detail by Dr. M. Stockdale in the International Journal of the Society of Cosmetic Scientists 9.1987.

The compositions were applied to the Luviset casts at an application rate of 1.5 mg/cm$^2$.

For compositions which do not interact with the Luviset cast the average of the zero time reading and the 10 minute reading is used. These readings are termed "the weighted cast SPF's".

Comparative sunscreen compositions were prepared from two fine particle size titanium dioxide products which were uncoated products obtainable under the names Teikoku Kako MT150W 0.015 micron rutile TiO$_2$ (Pigment X) and Deussa P25 anatase TiO$_2$ 0.03 micron (Pigment Y).

The compositions had the following ingredients with ingredients similar to those of compounds A, B and C having the same item numbers.

| | Compositions % weight | | | | | |
|---|---|---|---|---|---|---|
| ITEM | D | E | F | G | H | I |
| 1 | 15.0 | 5.0 | 10.0 | 10.0 | 15.0 | 5.0 |
| 2 | 2.0 | 2.0 | 2.0 | 2.0 | 2.0 | 2.0 |
| 3 | 4.0 | 2.0 | 3.0 | 3.0 | 3.0 | 2.0 |
| 4 | 1.0 | 1.0 | 1.0 | 1.0 | 1.0 | 1.0 |
| 5 | 3.0 | 3.0 | 3.0 | 3.0 | 3.0 | 3.0 |
| 7 | 50.0 | 80.75 | 68.5 | 68.5 | 50.0 | 80.75 |
| isopropyl palmitate | 15.0 | 3.75 | 7.5 | 7.5 | 15.0 | 3.75 |
| Pigment X | 10.0 | 2.5 | 5.0 | | | |
| Pigment Y | | | | 5.0 | 10.0 | 2.5 |
| % TiO$_2$ | 10 | 2.5 | 5.0 | 5.0 | 10.0 | 2.5 |

The sunscreen compositions were prepared in a similar manner to that employed for compositions A, B and C and all the ingredients except items 5 and 7 were milled together initially. The pigments were in the dry state.

The weighted cast SPF measurement were determined on all the comparative products and also on the base formulations employed for the 2.5% TiO$_2$ sunscreen and also for the 10% TiO$_2$ sunscreen. A standard sunscreen preparation (DIN 67501 1984) was also tested and the results are given below

| Composition | Weighted Cast SPF |
|---|---|
| A. | 8.3 ± 1.5 |
| F. | 2.3 ± 0.2 |
| G. | 4.9 ± 0.4 |
| B. | 13.5 ± 3.8 |
| D. | 6.8 ± 0.7 |
| H. | 10.4 ± 4.1 |
| C. | 2.4 ± 0.3 |
| E. | 1.5 ± 0.1 |
| I. | 1.8 ± 0.1 |
| 2.5% Base | 1.1 ± 0.0 |
| 10% Base | 1.1 ± 0.0 |
| Standard (DIN) | 3.3 ± 0.5 | the actual readings at 0 minutes and 10 minutes and the number of casts are given for the in vitro determinations:

| | SPF value after | | No of casts |
|---|---|---|---|
| Composition | 0 mins | 10 mins | |
| A. | 10.0 ± 1.8 | 6.6 ± 1.6 | 10 |
| F. | 2.8 ± 0.2 | 1.9 ± 0.1 | 10 |
| G. | 5.6 ± 0.4 | 4.2 ± 0.4 | 10 |
| B. | 14.1 ± 3.7 | 12.9 ± 4.5 | 10 |
| D. | 7.6 ± 0.7 | 5.9 ± 1.3 | 10 |
| H. | 12.5 ± 5.9 | 8.2 ± 2.6 | 10 |
| C. | 2.8 ± 0.2 | 1.9 ± 0.4 | 10 |
| E. | 1.6 ± 0.1 | 1.3 ± 0.1 | 10 |
| I. | 1.9 ± 0.1 | 1.7 ± 0.1 | 10 |
| 2.5% Base | 1.1 ± 0.0 | 1.0 ± 0.0 | 10 |
| 10% Base | 1.1 ± 0.0 | 1.0 ± 0.0 | 10 |
| Standard (DIN) | 3.1 ± 0.0 | 3.4 ± 0.6 | 24 |

These readings were analysed statistically and the results of the analysis given below

| Comparison | No. Degrees of freedom | t-Statistic | Probability |
|---|---|---|---|
| EvI | 18 | −8.28 | P < 0.001* |
| EvC | 18 | −9.83 | P < 0.001* |
| IvC | 18 | −6.09 | P < 0.001* |
| AvG | 18 | 7.13 | P < 0.001* |
| AvF | 18 | 12.92 | P < 0.001* |
| GvF | 18 | 20.84 | P < 0.001* |
| DvB | 18 | −5.48 | P < 0.001* |
| DvH | 18 | −2.74 | P < 0.02* |
| BvH | 18 | 1.74 | P > 0.05** |

*significant
**not significant

From the results obtained the mean of the individual weighted SPF's were calculated for each product and plotted against the percentage of titanium dioxide present within the formulation. This graph is shown in FIG. 1 of the attached drawings. In the graph the values X were from the products of this invention, 0 for pigment Y and Δ for Pigment X. The regression lines was drawn from the weighted cast values for each test product and this line takes into account the SPF of 1.1 for the base formulation.

From the graph, it can be seen that the weighted cast SPF was directly proportional to the concentration of titanium dioxide irrespective of the type of titanium dioxide.

The graph also shows that the product of the invention was more efficient at preventing the transmission of UV light than Pigment Y and this in turn was more efficient than Pigment X.

the emulsion bases for the 2.5% and 10% titanium dioxide formulations were evaluated and gave results which indicate that the base formulation had no ability to screen UV light. Thus the SPF's reported for the titanium dioxide emulsions were totally attributed to the titanium dioxide. With the results for these two samples being similar, there was no need to evaluate the base for the 5% emulsion.

From the statistical analyses it can be seen that at the 2.5% and 5% levels, the three titanium dioxide materials were significantly different from each other in their abilities at screening UV light (P>0.001). At the 10% titanium dioxide level, the new product was significantly better than Pigment X and was also better than Pigment Y although not significantly statistically different (P>0.05).

The results of these tests have shown that the three different types of titanium dioxide tested are not similar in their ability to screen UV light and the new product has important advantages in this respect.

I claim:

1. Particulate material comprising non-calcined titanium dioxide the particles of which are acicular in shape and which have a ratio of the longest dimension to the shortest dimension within the range of 8:1 to 2:1 and wherein the largest dimension is within the range 0.01 to 0.15 micron and said particles having a coating comprising an oxide or hydrous oxide of aluminum and an oxide or hydrous oxide of silicon in a weight ratio of $Al_2O_3:SiO_2$ of at least 1.5 and not greater than 4.5 and said material being substantially transparent to visible light and substantially absorbant to UV light.

2. Particulate material according to claim 1 in which the largest dimension is within the range 0.02 to 0.1 micron.

3. Particulate material according to claim 1 in which at least 80 per cent of the particles have a size within the range 0.1 to 0.15 micron.

4. Particulate material according to claim 1 in which the amount of oxide or hydrous oxide of aluminium when expressed as $Al_2O_3$ is from 1.0 to 30.0 per cent based on the weight of titanium dioxide.

5. Particulate material according to claim 1 in which the amount of said oxide or hydrous oxide of aluminium is from 5 to 20 per cent by weight $Al_2O_3$ on titanium dioxide.

6. Particulate material according to claim 1 in which the amount of the oxide or hydrous oxide of silicon is within the range of 0.2 to 20.0 weight percent as $SiO_2$ on titanium dioxide.

7. Particulate material according to claim 1 in which the amount of the oxide or hydroxide of silicon is within the range 1.5 to 7.0 weight per cent.

8. Particulate material according to claim 1 in which the weight ratio $Al_2O_3:SiO_2$ in the coating is from 2.0 to 3.5.

9. Particulate material according to claim 1 in which the particles carry a coating of an organic compound selected from the class consisting of organic silicon compounds, polyols, amines and alkanolamines.

10. Particulate material according to claim 1 in which the particles carry an organic dispersing agent selected from the class consisting of substituted carboxylic acids and soap bases.

11. Particulate material according to claim 1 in which the particles carry a substituted carboxylic acid which is a hydroxy carboxylic acid.

12. Particulate material according to claim 1 in which the particles carry a polyhydroxy stearic acid.

13. Particulate material according to claim 1 in which the particles of titanium dioxide have a purity such that the amount of sulphate expressed as $SO_3$ present in them does not exceed 0.9% by weight of the particles free of coating oxides or hydrous oxides.

14. A method for the manufacture of a particulate material which comprises forming an aqueous dispersion of titanium dioxide the particles of which are acicular in shape and which have a ratio of the longest dimension to the shortest dimension within the range 8:1 to 2:1 and wherein the largest dimension is within the range 0.01 to 0.15 micron and which has not undergone any intervening calcination process, mixing the dispersion with a hydrolysable compound of aluminum and a hydrolysable compound of silicon to deposit on said particles a coating of a hydrous oxide of aluminum and a hydrous oxide of silicon in a weight ration of $Al_2O_3:SiO_2$ of at least 1.5 and not greater than 4.5 and drying the resultant product at a temperature substantially below calcination temperature.

15. A method according to claim 14 in which an aqueous dispersion of titanium dioxide is prepared by hydrolysing a hydrolysable titanium compound to precipitate said acicular particles.

16. A method according to claim 14 in which an aqueous dispersion of titanium dioxide is prepared by hydrolysing an inorganic titanate.

17. A method according to claim 14 in which an aqueous dispersion of titanium dioxide is milled to produce particles of the said dimensions prior to mixing with said hydrolysable compounds of aluminium and silicon.

* * * * *